United States Patent [19]

Koizumi et al.

[11] Patent Number: 4,963,027
[45] Date of Patent: Oct. 16, 1990

[54] OPTICAL FIBER CONNECTOR AND OPTICAL DENSITY MEASURING SYSTEM

[75] Inventors: Takashi Koizumi; Tadashi Uekusa, both of Kanagawa, Japan

[73] Assignee: Fuji Photo Film Co., Ltd., Kanagawa, Japan

[21] Appl. No.: 363,826

[22] Filed: Jun. 9, 1989

[30] Foreign Application Priority Data

Jun. 10, 1988 [JP] Japan ................. 63-142959

[51] Int. Cl.5 .................. G01N 21/00; G02B 6/36
[52] U.S. Cl. ..................................... 356/416; 356/419;
356/36; 350/96.15; 350/96.18; 350/96.21
[58] Field of Search ............... 356/402, 414, 416, 417, 356/418, 419; 250/226; 350/96.15, 96.21, 96.18

[56] References Cited
U.S. PATENT DOCUMENTS 3,697,185  10/1972  Kassel et al. ................. 356/418
4,061,428  12/1977  Amano et al. ................. 356/418
4,261,640   4/1981  Stankos et al. ............... 350/96.15
4,717,234   1/1988  Barlow et al. ................ 350/96.15

Primary Examiner—F. L. Evans
Attorney, Agent, or Firm—Sughrue, Mion, Zinn, Macpeak & Seas

[57] ABSTRACT

An optical density measuring system has a light projecting system which includes a light source and an optical fiber bundle which transmits light emitted from the light source to the specimen. The optical fiber bundle consists of first and second portions which are connected by an optical fiber connector. The connector includes a first optical fiber plug which holds the light emanating end face of the first portion of the bundle, a second optical fiber plug which holds the light incident end face of the second portion of the bundle, a plug holder which can be mated with both the first and second optical fiber plugs in such a manner that the light emanating end face of the first portion and the light incident end face of the second portion are closely opposed to each other, and an optical filter which transmits only light having a selected wavelength and is mounted on the plug holder in a position in which the optical filter is interposed between the light emanating end face of the first portion and the light incident end face of the second portion.

4 Claims, 4 Drawing Sheets

OPTICAL FIBER CONNECTOR AND OPTICAL DENSITY MEASURING SYSTEM

BACKGROUND OF THE INVENTION

1. Field of the Invention

This invention relates to an optical fiber connector which transmits only light having selected wavelengths, and an optical density measuring system in which the optical fiber connector is employed.

2. Description of the Prior Art

Quantitative or qualitative analysis of a specific component in a sample liquid is a common operation carried out in various industrial fields. Especially, quantitative analysis of a chemical component or a solid component contained in body fluid such as blood or urine is very important in the field of clinical biochemistry.

There has been put into practice a dry-type chemical analysis slide with which a specific component contained in a sample liquid can be quantified through a droplet of the sample liquid deposited on the slide. See Japanese Patent Publication No. 53(1978)-21677, Japanese Unexamined Patent Publication No. 55(1980)-164356 or the like. When such a dry-type chemical analysis slide is used, the sample liquid can be analyzed more easily and more quickly than when the conventional wet analysis method is used, and accordingly the dry-type chemical analysis slide is very convenient for medical facilities, laboratories and the like where lots of sample liquids have to be analyzed.

When chemical components or the like contained in a sample liquid is analyzed using such a dry-type chemical analysis slide, a droplet of the sample liquid is deposited on the slide and is held at a constant temperature for a predetermined time in an incubator so that coloring reaction occurs, and the optical density of the color formed by the coloring reaction is optically measured. That is, measuring light containing a wavelength which is pre-selected according to the combination of the component to be analyzed and the reagent contained in the reagent layer of the slide is projected onto the slide and the optical density of the reflected light is measured. Then the component to be analyzed is quantified on the basis of the optical density of the reflected light by colorimetry.

In medical facilities, laboratories and the like where lots of sample liquids are analyzed, it is preferred that a plurality of sample liquids can be analyzed automatically and sequentially. Accordingly, there have been proposed various systems for sequentially effecting analysis of a plurality of sample liquids using the dry-type chemical analysis slides, as disclosed in Japanese Unexamined Patent Publication No. 56(1981)-777746, for instance. Further, there has been proposed in U.S. Pat. No. 3,526,480 a system which enables automatic and sequential analysis of a plurality of sample liquids by the use of a test film in a continuous length bearing thereon a reagent layer. In the system, the deposition of droplets of a plurality of sample liquids on the test film, the incubation of the droplets, and the measurement of the optical density of the reflected light are sequentially carried out while the test film is intermittently conveyed. The system using the test film in continuous length is advantageous over the system using the slides in that the running cost is lower and lots of sample liquids can be sequentially analyzed with a simple mechanism.

In the biochemical analysis system using either the slides or the test film, the optical density of the reflected light is measured with a reflection density measuring system. The reflection density measuring system generally comprises a light projecting means which projects measuring light onto a specimen, and a photodetector which detects light reflected at the specimen. As the light projecting means, there has been known one which comprises a light source and an optical fiber means which transmits light emitted from the light source to the specimen. (See Japanese Unexamined Patent Publication No. 62(1987)-245241, for instance.) Such a light projecting means is advantageous in that the light emitted from a single light source can be projected onto a plurality of specimens at one time by the use of a plurality of optical fiber means, and the light source can be relatively freely positioned with respect to the position of the specimens.

The light source generally comprises a tungsten lamp which emits light having a relatively wide wavelength range. On the other hand, the wavelength most effective to the measurement differs depending on the component of the sample liquid to be analyzed. That is, when light having a particular wavelength is projected onto the specimen, the change in the quantity of the reflected light from the specimen with change of the concentration of a given component in the sample liquid is maximized, and the particular wavelength of the light which causes the maximum change in the quantity of the reflected light changes depending on the kind of the component in the sample liquid. For example, the "particular wavelength" for glucose is about 510 nm. When only light having the particular wavelength is projected onto the specimen according to the given component to be analyzed in the specimen, the concentration of the component can be measured most effectively. Light having a selected wavelength can be projected onto the specimen by the use of an optical filter which transmits only the light having the selected wavelength. The optical filter may be an interference filter, for instance, and may be disposed near the light source or the light emanating end of the optical fiber means, for instance.

Since, there are a plurality of components to be analyzed and in order to effectively accomplish the measurement of the optical density, the optical filter must be changed according to the component to be analyzed. However, the part of the reflection density measuring system near the light source and the part near the light emanating end to the optical fiber means are generally difficult of access.

SUMMARY OF THE INVENTION

In view of the foregoing observations and description, the primary object of the present invention is to provide an optical density measuring means in which the wavelength of the measuring light to be projected onto the specimen can be changed easily.

Another object of the present invention is to provide an optical fiber connector which is useful to change the wavelength of the measuring light to be projected onto the specimen in an optical density measuring means.

In accordance with one aspect of the present invention, there is provided an optical fiber connector for connecting a first and second optical fiber means, each having a light incident end face through which light enters the optical fiber means and a light emanating end face through which the light emanates from the optical fiber means. The connector comprises a first optical fiber plug which holds the light emanating end face of the first optical fiber means, a second optical fiber plug which holds the light incident end face of the second optical fiber means, a plug holder which can be mated with both the first and second optical fiber plugs in such a manner that the light emanating end face of the first optical fiber means and the light incident end face of the second optical fiber means are closely opposed to each other, and an optical filter which transmits only light having a selected wavelength and is mounted on the plug holder in a position in which the optical filter is interposed between the light emanating end face of the first optical fiber means and the light incident end face of the second optical fiber means.

In accordance with another aspect of the present invention, there is provided an optical density measuring system having a light projecting means which comprises a light source and an optical fiber means which transmits light emitted from the light source to the specimen and comprises a first and second optical fiber means connected by the optical fiber connector of the present invention.

The plug holder can be easily replaced with another plug holder having desired light transmission properties so that light the wavelength of which is in a desired wavelength range is only transmitted through the filter and projected onto the specimen.

DESCRIPTION OF THE PREFERRED EMBODIMENT

Figure 1:
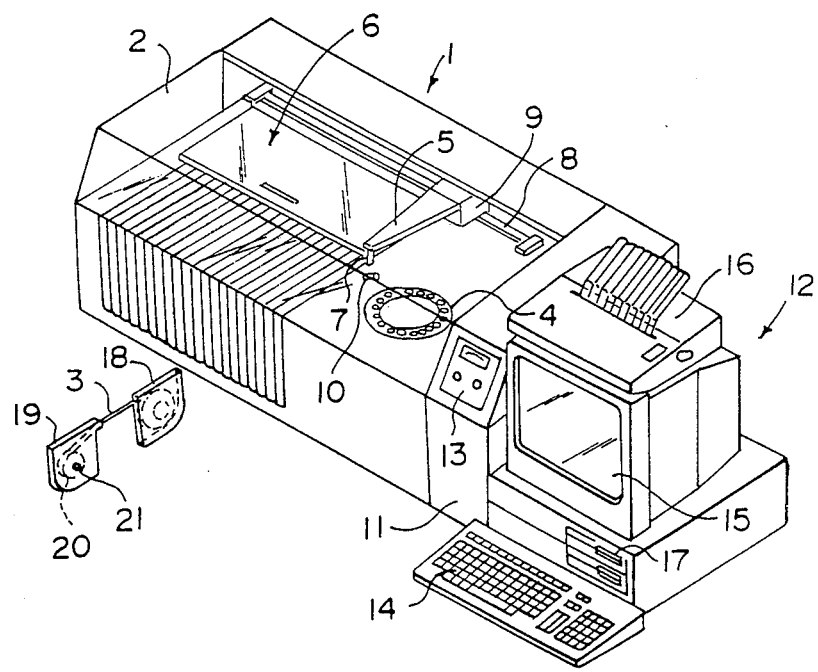
FIG. 1 is a perspective view of a biochemical analysis system provided with an optical density measuring system in accordance with an embodiment of the present invention.

In FIG. 1, a biochemical analysis system 1 has a transparent lid 2. While the lid 2 is opened, test tapes (test films in a continuous length) 3, sample liquids, and the like are accommodated in the system 1 and taken out therefrom. A sample liquid container 4 having a plurality of sample liquid wells arranged in a circle is provided in the system 1, and the sample liquids put in the wells are taken up therefrom and deposited on the test tape 3 by a depositing means 5 as will be described later. In this particular embodiment, a plurality of test tapes 3 bearing thereon different reagent layers each of which causes coloring reaction with a particular chemical component or solid component in the sample liquid are prepared. Each test tape 3 is provided in the form of a cassette which comprises a tape supply casing 18 and a tape take-up casing 19. The virgin part of the test tape 3 is rolled in the tape supply casing 18 and the used part of the tape 3 is wound around a take-up reel 20 in a tape take-up casing 19. The take-up reel 20 is provided with a central opening 21 which is engaged with an output shaft of a motor for drawing out the tape 3 from the supply reel 18 as will be described later. The cassettes are arranged in a row in a tape receiving section 6 with the tape supply casing 18 and the tape take-up casing 19 for each tape 3 being spaced from each other so that a part of the virgin part of the tape 3 is exposed between the casings 18 and 19.

The depositing means 5 comprises a driving mechanism 9 which supports a depositing nozzle 7 and moves along a rail 8. The nozzle 7 is moved along the row of the tapes 3 by the driving mechanism 9 carrying one of the sample liquids taken up from the sample liquid container 4 and deposits it on the exposed part of one of the tapes 3 as will be described in more detail later. The driving mechanism 9 also moves the nozzle 7 up and down, and the nozzle 7 is held in the upper position when it is moved along the row of the tapes 3, and is moved downward when it takes out the sample liquid, when it deposits it on the tape 3, and when it is washed.

The nozzle 7 is washed at a nozzle washing section 10 disposed between the tape receiving section 6 and the sample liquid container 4 after deposition of the sample liquid on the tape 3 in order to prepare for the next deposition.

The tape 3, deposited with the sample liquid is incubated in an incubator and the reflection density of the tape 3 is measured at an optical density measuring section as will be described later.

A computer 12 connected to a circuit portion 11 controls the whole system 1 and processes data obtained. A power switch, an ammeter and the like are disposed on a front panel 13 which is provided in front of the circuit portion 11. The computer 12 is provided with a key board 14 for giving command to the biochemical analysis system 1, a CRT display 15 which displays auxiliary information useful for the command, result of the ,measurement or the like, a printer 16 which prints out the result of the measurement and a floppy disk device 17 which stores the commands given to the system 1, data on the result of the measurement, and the like.

Figure 2:
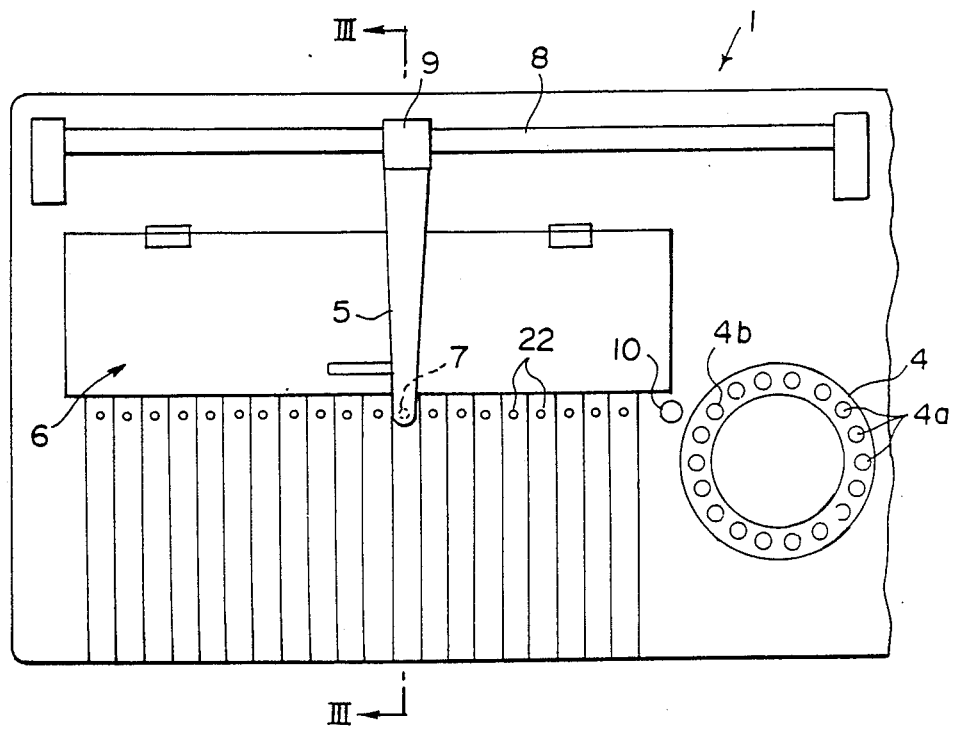
FIG. 2 is a fragmentary plan view showing a part of the biochemical analysis system.

As clearly shown in FIG. 2, the tape cassettes are positioned in the tape receiving section 6 so that the exposed parts 22 of the tapes 3 at which the sample liquid is deposited on the tapes 3 are arranged in a line, and the nozzle washing section 10 and a sample liquid take-up position 4b of the sample liquid container 4 are positioned on the line.

Said sample liquid wells of the sample liquid container 4 arranged in a circle are indicated at 4a in FIG. 2. The container 4 is automatically rotated by a driving means (not shown) so that the well 4 containing therein the sample liquid which is used in the next measurement is brought to the sample liquid take-up position 4b. In order to prevent a change of properties of the sample liquids due to evaporation, the wells 4a are covered with caps (not shown) except the one positioned in the sample liquid take-up position 4b.

The depositing means 5 takes up the sample liquid in the well 4a positioned in the take-up position 4b and deposits it on the tape 3 at the exposed parts 22.

Figure 3:
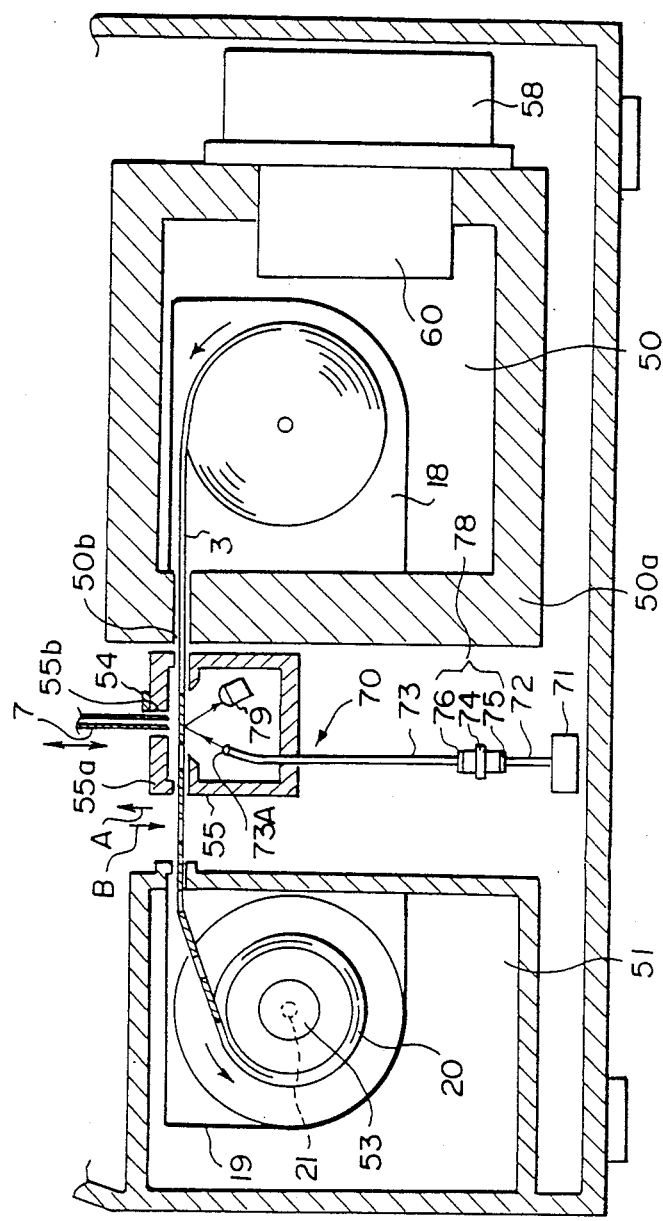
FIG. 3 is a cross-sectional view taken along line III—III in FIG. 2.

As shown in FIG. 3, the tape supply casing 18 of each tape cassette is placed in a refrigerator 50 the space in which is kept at 4° C., for instance, and the tape take-up casing 19 is placed in a tape take-up chamber 51. Since the virgin part of the tape 3 is accommodated in the casing 18, the virgin part of the tape 3 can be placed in the refrigerator 50 without touching it. The refrigerator 50 has walls 50a formed of heat insulation material, and an air-conditioner 58 which keeps the inside of the refrigerator at a low temperature and a low humidity is mounted on one of the walls 50a. A fan 60 circulates the air in the refrigerator 50.

A take-up motor 53 is disposed in the tape takeup chamber 51, and when the tape take-up casings 19 are placed in the tape take-up chamber 51, the output shaft of the motor 53 is brought into engagement with the central openings 21 of the reels 20. The test films 3 are drawn out through the outlet 50b of the refrigerator 50 and taken up around the reels 20 in response to rotation of the motor 53.

Since the used part of each test tape 3 is taken up in the casing 19, the tape 3 can be thrown without touching the used tape contaminated with the sample liquid. Instead of being taken up in the casing 19, the used tape 3 may be cut and collected in a box which is demountably mounted on the system 1 and is thrown together with the used tape cuttings collected therein. In this case, the test tapes 3 are drawn by pinch rollers, for example.

The test tapes 3 are conveyed through an incubator 55 which is disposed between the refrigerator 50 and the tape take-up chamber 51. An optical density measuring system 70 which measures the optical density of the color formed by the coloring reaction which occurs on the test tape 3 is disposed inside of the incubator 55 and below the incubator 55.

Figure 4:
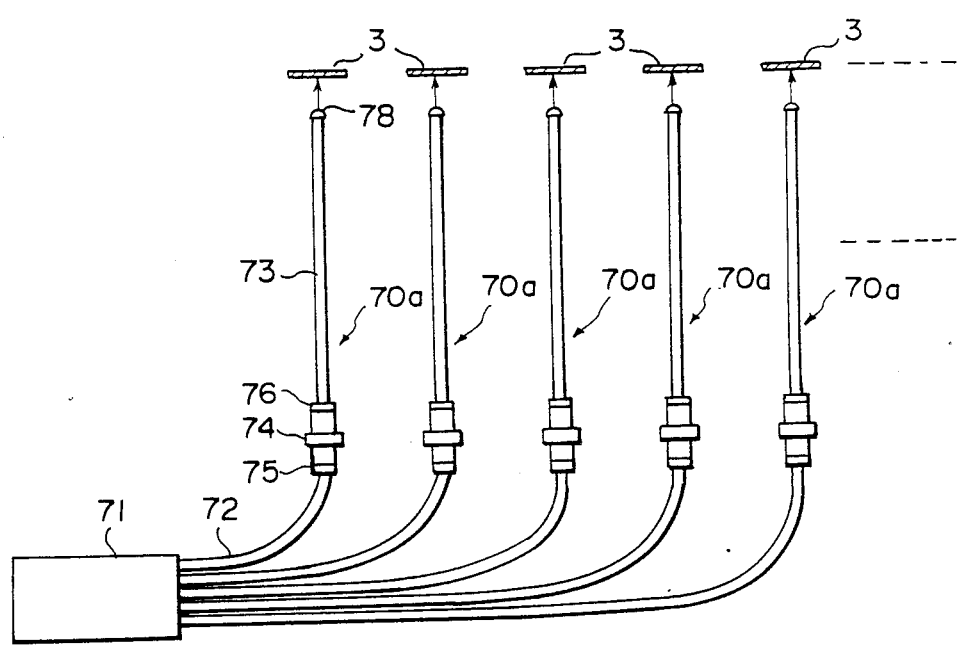
FIG. 4 is a schematic front view of the optical density measuring system.

The test tape 3 is intermittently drawn out from the refrigerator 50 and conveyed leftward (as seen in FIG. 3) driven by the motor 53. The incubator 55 has a lid which is movable up and down as shown by arrows A and B, and is provided with a nozzle hole 55b which gives the nozzle 7 of the depositing means 5 access to the tape 3 and is normally closed by a shutter 54. When the tape 3 is conveyed, the lid 55a is moved upward, and after the tape 3 is conveyed by a predetermined distance, the lid 55a is lowered and holds the tape 3. Then the shutter 54 is moved rightward and opens the nozzle hole 55b. Thereafter, the nozzle 7 is moved downward and deposits the sample liquid on the tape 3 through the nozzle hole 55b. Then the nozzle 7 is moved upward away from the lid 55a and the shutter 54 closes the nozzle hole 55b in order to prevent ventilation. Thereafter, the inside of the incubator is kept at a predetermined temperature (e.g., 37° C.). The portion of the test tape 3 on which the sample liquid is spread (the hatched portions in FIG. 3) incubated at a constant temperature for a predetermined time (e.g., four minutes) in the incubator 55. After the incubation or during the incubation, the optical density of the portion of the tape 3 on which the sample liquid is spread is measured by the optical density measuring system 70. That is, light emitted from a light source 71 is transmitted through a light transmitting means 70a which comprises a first optical fiber means 72 and a second optical fiber means 73 connected by an optical fiber connector 78 and is projected on the part of the tape 3 to be measured, and reflected light from the tape 3 is detected by a photodetector 79. The second optical fiber means 73 is provided at the light emanating end face thereof with a lens 73A which condenses the light emanating from the second optical fiber means 73 into a light beam having a predetermined diameter The optical density measuring system 70 is provided with one light transmitting means 70a and one photodetector 79 for each of the test tapes 3 in the tape receiving section 6 as shown in FIG. 4. All the first optical fiber means 72 are connected to a single light source 71. The light source 71 comprises a tungsten lamp, for instance, and emits light having a relatively wide wavelength range. The light which is emitted from the light source 71 and enters each of the first optical fiber means 72 through the end face adjacent to the light source 71 travels through the first optical fiber means 72 and enters the second optical fiber means 73 by way of the optical fiber connector 78. The optical fiber connector 78 comprises a first optical fiber plug 75 which holds the light emanating end face of the first optical fiber means 72, a second optical fiber plug 76 which holds the light incident end face of the second optical fiber means 73, and a plug holder 74 which is mated with both the first and second optical fiber plugs 75 and 76.

Figure 5:
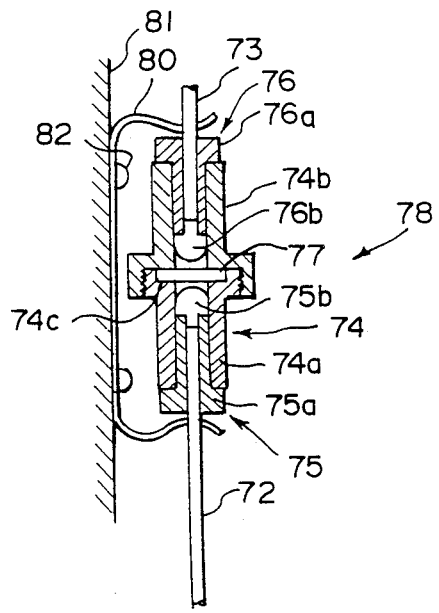
FIG. 5 is a cross-sectional view of the optical fiber connector.

As shown in FIG. 5, the first optical fiber plug 75 comprises a first plug body 75a which holds the first optical fiber means 72 and a lens 75b which collimates the light emanating from the first optical fiber means 72. The second optical fiber plug 76 comprises a second plug body 76a which holds the second optical fiber means 73 and a lens 76b which is disposed on the light incident end face of the second optical fiber means 73 and condenses the collimated light emanating from the first optical fiber means 72 before it enters the second optical fiber means 73. The plug holder 74 comprises first and second portions 74a and 74b. The first portion 74a is a tubular member having a passage into which the first optical fiber plug 75 is fitted and has a recess 74c on the upper end thereof. A interference filter 77 which has desired light transmission properties selected according to the kind of the component to be analyzed is seated in the recess 74c. The second portion 74b is a tubular member having a passage into which the second optical fiber plug 76 is fitted. The first portion 74a is screwed into the second portion 74b, and when the former is screwed into the latter, the lower end face of the latter holds the interference filter 77 seated in the recess 74c. The plug holder 74 holds the first and second optical fiber plugs 75 and 76 in such a manner that they are opposed to each other with the interference filter 77 intervening therebetween. After the plugs 75 and 76 are fitted into the holder 74, the plugs 75 and 76 are retained there by a retainer 80 which may comprise a plate spring, for instance.

As clearly shown in FIG. 5, in the plug holder 74, the light emanating end face of the first optical fiber means 72 and the light incident end face of the second optical fiber means 73 are closely opposed to each other with the interference filter 77 intervening therebetween. The light emanating from the first optical fiber means 72 is filtered by the filter 77 and only light having a predetermined wavelength passes through the filter 77 and projected onto the test tape 3. A plurality of plug holders 74 provided with different filters 77 are prepared and one of the holders 74 is used according to the component to be analyzed. When the filter 77 is interposed between the light emanating end face of the first optical fiber means 72 and the light incident end face of the second optical fiber means 73, the distance between the end faces is inherently increased. Accordingly, it is preferred that the lenses 75a and 76b be provided in order to prevent deterioration of the light transmission efficiency.

In the case where the filter 77 in the plug holder 74 can be easily replaced as in this embodiment, only the filter may be replaced instead of replacing the whole plug holder 74. The filter need not be limited to the interference but various other filters may be used.

After the measurement of the optical density, the tape 3 is kept there until another sample liquid is deposited. That is, the tape 3 is conveyed by a predetermined distance so that a new part is exposed between the casing 18 and 19 immediately before another sample liquid is deposited on the tape 3.

Though, in the embodiment described above, the optical density measuring system is arranged so that it measures the optical densities of a plurality of test tapes at one time, it may be arranged to measure the optical density of a single test tape at one time. Further, chemical analysis slides may be used as the specimen. Further, the present invention may be applied to the optical density measuring system which measures the optical density of the light transmitted through the specimen.

We claim:

1. An optical fiber connector for connecting a first and second optical fiber means, each having a light incident end face through which light enters the optical fiber means and a light emanating end face through which the light emanates from the optical fiber means comprising;

a first optical fiber plug which holds the light emanating end face of the first optical fiber means, a second optical fiber plug which holds the light incident end face of the second optical fiber means, a plug holder which is mated with both the first and second optical fiber plugs in such a manner that the light emanating end face of the first optical fiber means and the light incident end face of the second optical fiber means are closely opposed to each other, and a stationary optical fiber which transmits only light having a selected wavelength and is directly mounted on the plug holder in a position in which the optical filter is interposed between the light emanating end face of the first optical fiber means and the light incident end face of the second optical fiber means, wherein each of said light emanating end face of the first optical fiber means and said light incident end face of the second optical fiber means has a lens provided thereon.

2. The optical fiber connector according to claim 1, further comprising a plate spring retainer for retaining said first and second optical fiber plugs in said plug holder.

3. An optical density measuring system for measuring an optical density of a specimen comprising a light projecting means which projects light onto the specimen, a photodetector which detects light reflected from the specimen or light transmitted through the specimen and an incubator which houses said specimen and said photodetector, said light projecting means having a light source and an optical fiber means which transmits light emitted from the light source to the specimen, said optical fiber means having an end extending into said incubator, wherein:

said optical fiber means comprises first and second optical fiber means, each having a light incident end face through which light enters the optical fiber means and a light emanating end face through which the light emanates from the optical fiber means, and an optical fiber connector which connects the first and second optical fiber means, the optical fiber connector comprising a first optical fiber plug which holds the light emanating end face of the first optical fiber means, a second optical fiber plug which holds the light incident end face of the second optical fiber means, a plug holder which is mated with both the first and second optical fiber plugs in such a manner that the light emanating end face of the first optical fiber means and the light incident end face of the second optical fiber means are closely opposed to each other, and a stationary optical filter which transmits only light having a selected wavelength and is directly mounted on the plug holder in a position in which the optical filter is interposed between the light emanating end face of the first optical fiber means and the light incident end face of the second optical fiber means.

4. The optical density measuring system according to claim 3, wherein a plurality of plug holders having different optical filters are prepared and whereby one of said plug holders is used according to a desired component which is analyzed.

* * * * *